United States Patent
Urbano et al.

(10) Patent No.: US 6,592,521 B1
(45) Date of Patent: Jul. 15, 2003

(54) MEDICAL DIAGNOSTIC ULTRASOUND SYSTEM AND METHOD FOR POWER CONTROL

(75) Inventors: Joseph A. Urbano, Audubon, PA (US); Christopher B. Knell, Morrestown, NJ (US); Michael G. Cannon, Haveford, PA (US); Anthony P. Lannutti, Norristown, PA (US)

(73) Assignee: Acuson Corporation, Mountain View, CA (US)

( * ) Notice: Subject to any disclaimer, the term of this patent is extended or adjusted under 35 U.S.C. 154(b) by 0 days.

(21) Appl. No.: 09/516,397

(22) Filed: Mar. 1, 2000

(51) Int. Cl.7 .................................................. A61B 8/00
(52) U.S. Cl. ........................ 600/441; 600/437; 600/447; 73/627
(58) Field of Search .................................. 600/437, 449, 600/459, 460, 461, 447; 73/627, 628; 378/101, 102; 307/66

(56) References Cited

U.S. PATENT DOCUMENTS

| | | | |
|---|---|---|---|
| 5,640,960 A | * 6/1997 | Jones et al. | 600/437 |
| 5,690,114 A | 11/1997 | Chiang et al. | |
| 5,722,412 A | 3/1998 | Pflugrath et al. | |
| 5,748,103 A | 5/1998 | Flach et al. | |
| 5,808,376 A | * 9/1998 | Gordon et al. | 307/66 |
| 5,827,969 A | * 10/1998 | Lee et al. | 73/627 |
| 5,867,561 A | * 2/1999 | Strasser et al. | 378/101 |
| 5,924,988 A | 7/1999 | Burris et al. | |

OTHER PUBLICATIONS

Tsi Power Corporation; Power Primer; Feb. 11, 2000; pp. 1–3.

* cited by examiner

Primary Examiner—Marvin M. Lateef
Assistant Examiner—Maulin Patel

(57) ABSTRACT

Methods and systems for providing consistent power and reducing power consumption for an ultrasound system are provided. The ultrasound system is provided with an uninterruptable power supply. Power is provided from an outlet through the uninterruptable power supply to the ultrasound scanner. If the power from the outlet falls below a threshold is of an insufficient quality or is otherwise unavailable, the uninterruptable power supply provides power. For mobility, the uninterruptable power supply provides power, avoiding the need to plug the ultrasound system into an outlet. To reduce the drain on the uninterruptable power supply or other source of power, the ultrasound system includes power reduction systems and methods. One or more electrical components, subsystems or the entire ultrasound system is operated in a reduced power state while not in use. For example, some digital electrical components draw more power in response to clock signal triggers. The clock signal provided to one or more digital electrical components is decreased in frequency or set to steady state, decreasing the amount of power used.

56 Claims, 1 Drawing Sheet

MEDICAL DIAGNOSTIC ULTRASOUND SYSTEM AND METHOD FOR POWER CONTROL

BACKGROUND

This invention relates to a medical diagnostic ultrasound system and method for power control. In particular, ultrasound methods and systems for providing power and reducing power consumption are provided.

Medical diagnostic ultrasound systems are used in a variety of locations, such as hospital emergency rooms, out-patient centers, and other medical offices. Ultrasound systems typically connect with an electrical outlet. Hand carried portable ultrasound systems or systems wheeled on carts allow movement of the system from one area to another within a medical office. For example, portable systems are hand carried from one location to another. Portable systems may be battery operated, such as disclosed in U.S. Pat. No. 5,640,960 or (Ser. No. 09/396,486, filed Sep. 14, 1999). These locations may be in well developed regions with dependable power supply infrastructures or lesser developed regions with erratic or undependable power supply infrastructures. The quality and consistency of the power depends on the location. Additionally, an ultrasound system may be needed in an area within a medical office that does not have convenient access to the power infrastructure.

BRIEF SUMMARY

The present invention is defined by the following claims, and nothing in this section should be taken as a limitation on those claims. By way of introduction, the preferred embodiment described below includes a method and system for providing consistent power to an ultrasound system and reducing the power consumption by the ultrasound system.

The ultrasound system is provided with an uninterruptable power supply. Power is provided from an outlet through the uninterruptable power supply to the ultrasound system. If the power from the outlet falls below a threshold is of an insufficient quality or is otherwise unavailable, the uninterruptable power supply provides power. For mobility, the uninterruptable power supply provides power, avoiding the need to plug the ultrasound system into an outlet.

To reduce the drain on the uninterruptable power supply or other source of power, the ultrasound system includes power reduction systems and methods. One or more electrical components, subsystems or the entire ultrasound system is operated in a reduced power state while not in use. For example, some digital electrical components draw more power in response to clock signal triggers. The clock signal provided to one or more digital electrical components is decreased in frequency or set to steady state, decreasing the amount of power used.

In a first aspect, a medical diagnostic ultrasound system for reducing power consumption is provided. An ultrasound data path comprises at least a first electrical component. An ultrasound processing control operatively connects with the ultrasound data path and comprises at least a second electrical component. A source of power operatively connects with the ultrasound data path and the ultrasound processing control. At least one of the first and second electrical components has a full power mode during use and a low power mode during at least one non-use period.

In a second aspect, a medical diagnostic ultrasound system for generating data for an ultrasound image of a region of a patient with a plurality of electrical components is provided. The plurality of electrical components comprise a transmit beamformer, a receive beamformer, at least one signal processor and a scan converter. This system has a power mode control path operatively connected with at least one of the plurality of electrical components. The electrical component is responsive to a signal from the power mode control path to change between a decreased power state and an increased power state.

In a third aspect, a medical diagnostic ultrasound method for reducing power consumption by an ultrasound system is provided. An ultrasound image is generated with the ultrasound system. At least one component of the ultrasound system is placed in a low power state.

In a fourth aspect, a medical diagnostic ultrasound system for uninterrupted power supply is provided. An ultrasound system comprising an ultrasound beamformer and an ultrasound signal processor is operatively connected with a power input. An uninterrupted power supply also operatively connects with the power input.

In a fifth aspect, a medical diagnostic ultrasound method for uninterrupted power supply to an ultrasound system is provided. An ultrasound scanner comprising an ultrasound beamformer and an ultrasound signal processor is powered. An uninterruptable power supply is powered from a power outlet. The ultrasound scanner is powered by the uninterruptable power supply.

Further aspects and advantages of the invention are discussed below in conjunction with the preferred embodiments.

DETAILED DESCRIPTION OF THE PREFERRED EMBODIMENTS

The embodiments discussed below include one or both of medical diagnostic ultrasound systems with uninterruptable power supplies or power reduction control circuits. Uninterruptable power supplies allow for use in various locations without depending on a source of power external to the ultrasound system. Power reduction control circuitry allows longer operation from an uninterruptable power supply or other battery device. Power reduction also decreases energy costs and reduces heat generated by the system.

Figure 1:
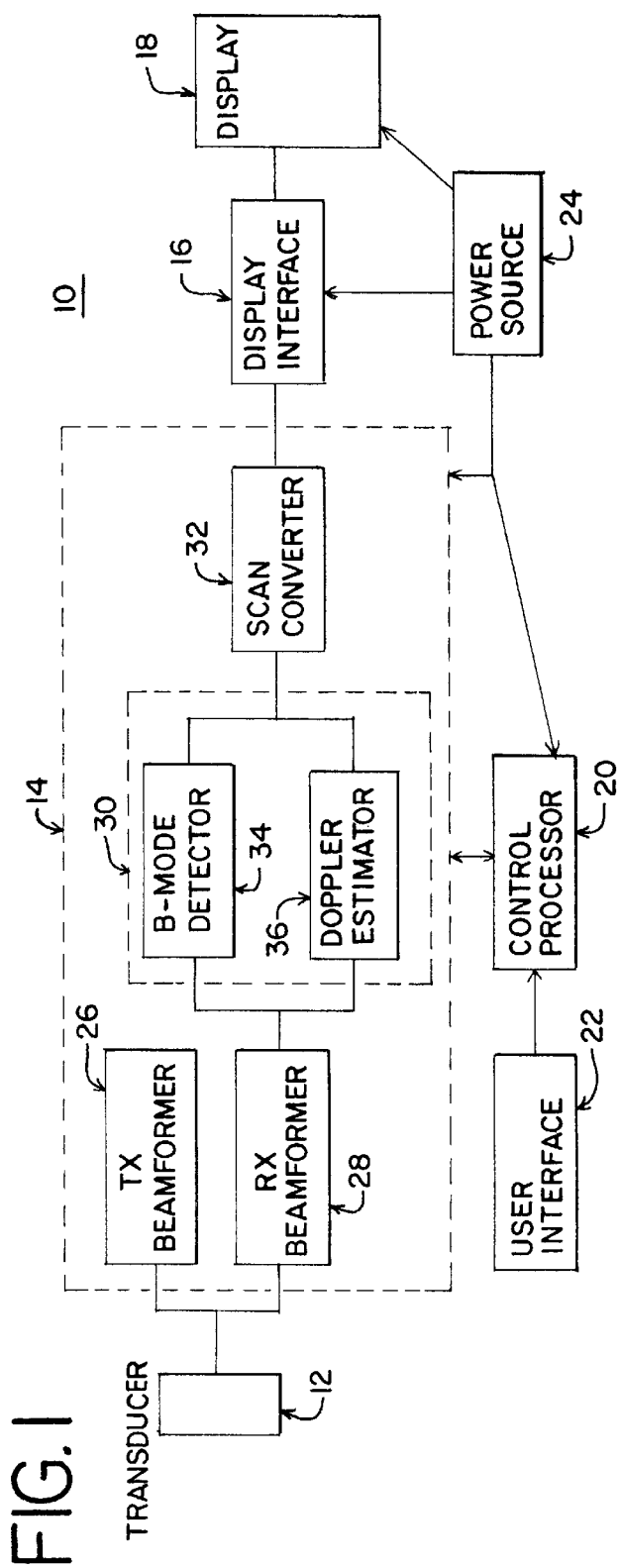
FIG. 1 is a block diagram of one embodiment of a medical diagnostic ultrasound system for power control.

FIG. 1 shows an ultrasound system 10. The ultrasound system includes a transducer 12, an acquisition module 14, a display interface 16, a display 18, a control processor 20, a user interface 22 and a power source 24. The system 10 comprises a medical diagnostic ultrasound system, such as manufactured by Acuson Corporation under the trade names Sequoia®, Aspen™, and 128XP®. For example, the ultrasound system 10 comprises an ultrasound system as disclosed in U.S. Pat. Nos. 5,685,308, 5,675,554, 5,581,517, 5,555,534 and 5,570,691, the disclosures of which are incorporated herein by reference. As yet another example, an ultrasound system as described in U.S. Pat. No. 5,971,923 may be used. Other ultrasound systems by other manufacturers may be used.

In one embodiment, the ultrasound system 10 comprises a portable ultrasound system, such as disclosed in U.S. Pat. Nos. 5,690,114, 5,722,412, and (Ser. No. 09/396,486, filed Sep. 14, 1999), the disclosures of which are incorporated herein by reference. Portable ultrasound systems are shaped and sized for hand carrying from one location to another. For example, these ultrasound systems 10 are lightweight and small.

The ultrasound system 10 includes an ultrasound data path and an ultrasound processing control. Power consumption by electrical components is reduced in one or both of the ultrasound data path and the ultrasound processing control.

The ultrasound data path comprises the transducer 12, the acquisition module 14, the display interface 16, and the display 18. The ultrasound data path generates transmit waveforms for conversion to acoustic waveforms by the transducer 12, receives acoustic echoes at the transducer 12, processes electrical signals responsive to the acoustic echoes, and generates an ultrasound image.

The acquisition module 14 of the ultrasound data path comprises one or more subsystems, such as a transmit beamformer 26, a receive beamformer 28, a signal processor 30 and a scan converter 32. Additional or fewer subsystems may be provided. As used herein, a subsystem includes any grouping of one or more electrical components for performing one or more functions of the ultrasound system 10. For example, the acquisition module 16 also comprises a subsystem. One electrical component may be included within a plurality of subsystems.

The transmit beamformer 26 comprises one or more digital and/or analog electrical components for generating a plurality of transmit waveforms to focus acoustic energy along a scan line. The receive beamformer 28 also comprises a plurality of analog and/or digital electrical components for converting electrical signals from the transducer 12 into samples or other information representing reflections from along the scan line. For example, the transmit and receive beamformers 26 and 28 include analog-to-digital converters, digital-to-analog converters, amplifiers, filters, delays and summers. The receive beamformer 28 may also include a bandpass filter or low pass filter and demodulator for selectively passing signals at one or more frequency bands (e.g. the transmitted fundamental frequency band or harmonics thereof).

The output of receive beamformer 28 is provided to the signal processor 30. The signal processor 30 comprises one or more subsystems, such as the B-mode detector 34 and the Doppler estimator 36. Other subsystems may be provided, such as a spectral Doppler system. The B-mode detector 34 comprises look-up table memory, comparators and processors for detecting an amplitude, envelope or power of the signals and dynamically compressing the information. The Doppler estimator 36 comprises a signal processor, comparator, delay (i.e. corner turning memory), clutter filter and other devices for estimating one or more of Doppler velocity, Doppler energy, Doppler variance. The signal processor 30 may also include various processors, filters and memories for applying spatial filtering, temporal filtering, frequency filtering, thresholding, or other signal processes.

The signal processed information in provided to the scan converter 32. The scan converter 32 comprises one or more memories, processors and look-up tables for converting ultrasound data in a polar coordinate format to a Cartesian coordinate format for display. The scan converter 32 also assigns color values to Doppler information, such as applying a user selected color table to the Doppler estimates.

The display interface 16 receives scan converted information from the acquisition module 14. The display interface 16 comprises a video card or other electrical components for generating video signals from the scan converted information. The display interface 16 may also include memories for overlaying graphical information with the ultrasound image information.

The display 18 comprises a cathode ray tube (CRT), monitor, a flat panel display (e.g., active matrix or passive matrix with or without back lighting) or other display device. The display 18 receives the video information from the display interface 16 and generates an ultrasound image, including any graphical information.

Like the electrical components of the ultrasound data path, the electrical components of the ultrasound processing control may operate in a reduced power mode. The processing control comprises the user interface 22 and the control processor 20. Alternatively or additionally, the processing control includes various local controls within the subsystems of the ultrasound data path. The processing control configures and/or otherwise controls the processing of the ultrasound data generated by the ultrasound data path.

The control processor 20 comprises one or more microprocessors and associated volatile and/or non-volatile memories. Additional devices and associated electrical components may be provided, such as integrated circuitry, interfaces to external systems, ports, disk drives, and other general control circuitry.

The user interface 22 comprises a track ball, a keyboard, a mouse, dedicated keys, software controlled keys, touch screens (e.g., such as a touch screen included on the display 18) or other user input devices.

In response to the user interface 22, data input from a disc drive or port, or stored data, the control processor 20 controls operation of the various subsystems and electrical components of the ultrasound system 10. For example, the acquisition module 14 is configured as a function of a user selected mode or display and type of transducer. Various configurations are known, such as a Doppler velocity image overlaid on a B-mode image. Other examples include any one or any combination of B-mode, Doppler and Doppler spectral images. Transmit and receive beamforming configuration parameters are selected as a function of the type of transducer, such as sector, Vector®, curved linear or linear. Signal processing is configured, such as selecting an amount of temporal and spatial filtering. The frequency of interest for imaging is selected, such as a fundamental frequency band or a harmonic band of the fundamental frequency band. Graphical information may be selected, such as various calculations to be performed by the control processor 20 or another processor based on the ultrasound data or other information. The control processor 20 also obtains stored ultrasound data from a memory, such as on a volatile or non-volatile image memory. The control processor 20 provides the image information to either the scan converter 32, the display interface 16 or the display 18.

The power source 24 comprises a cord and plug for insertion into an outlet. For example, a standardized outlet providing 120 or 210 volts is provided. A three-phased power source may also be used. In alternative embodiments, a specialized outlet and associated plug is provided. In yet other alternative embodiments, such as for a portable ultrasound system, the power source 24 comprises one or more batteries, an uninterruptable power supply, a solar or other fuel powered generator.

In one embodiment for reducing power consumption, one or more electrical components in one or more of the subsystems of the ultrasound system 10 operate in a reduced power mode. During use, the electrical component operates in a full power mode or an increased power state. During a non-use period, the electrical component may be controlled to operate in a low power mode or a decreased power state. For example, a digital electrical component is placed into a sleep state for low power consumption.

Electrical components comprise digital or analog components. For example, electrical components comprise general processors operating pursuant to software control, digital signal processors, integrated circuits, application specific integrated circuits, field programmable gate arrays, microprocessors, analog amplifiers, analog-to-digital converters, digital-to-analog converters, random access memories (e.g., static random access memory, dynamic random access memory or other random access memories whether synchronized or unsynchronized), read only memories, multipliers, summers, dividers, comparators or other analog or digital electrical components. Other electrical components include the CRT or flat panel display. In various embodiments, the electrical components as described in the patents incorporated by reference herein are used.

Figure 2:
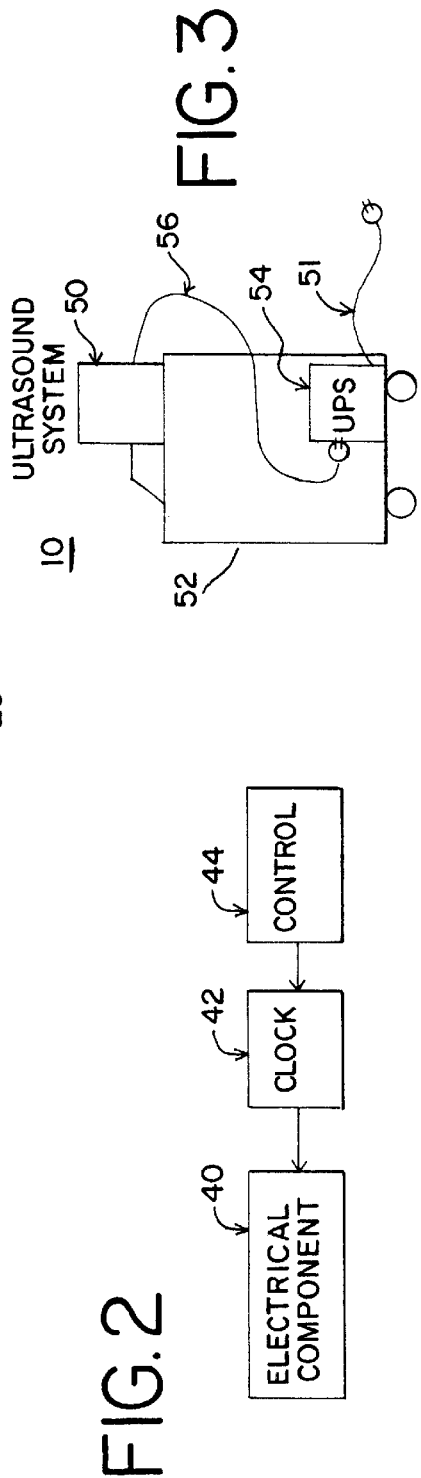
FIG. 2 is a block diagram of an embodiment of an electrical component and power mode control path for use in the system of FIG. 1.

FIG. 2 shows a control path for controlling the increased or decreased power state of an electrical component 40. In this embodiment, the control path comprises a clock 42 and a controller 44. The controller 44 controls the speed or frequency of the clock 42. In alternative embodiments, the control path comprises a controller internal or external to the electrical component.

Many digital electrical components, such as bipolar devices and complimentary metal-oxide semiconductor devices operate synchronously to a clock signal. Power consumption of the electrical component 40 correlates to the frequency of the synchronizing clock signal. When the clock signal toggles at a low frequency or is steady state, very little power is consumed. When the clock 42 outputs a clock signal at a standard operating frequency, such as 10 to 500 MHz, the electrical component 40 operates in a full power mode or increased power state. A lesser or greater frequency may be provided for standard operation of the electrical component 40. A standard operating clock frequency is used for operation of the electrical component 40, such as for processing ultrasound data with the electrical component 40. When the electrical component 40 is not being used, the control 44 controls the output of the clock to halt or reduce the toggling rate, reducing consumption of power by the electrical component 40.

Other electrical components have a suspended or standby mode of operation. A suspend or standby mode comprises a decreased power state or low power load mode. For example, a microprocessor, such as the Cyrix Media GX, enters the decreased power state in response to an instruction or an external signal. Other examples of electrical components that include a suspend or standby mode are analog to digital converters, digital analog converters and static random access memories. Other electrical components may incorporate suspend or standby modes activated by an instruction or external signal. In these embodiments, the control path comprises a controller for generating the external suspend or standby signal. Alternatively, the electrical component includes a time-based or other internal instruction for automatically entering a suspend or standby mode during periods of nonusage. As an alternative or in addition to using a suspend or standby feature, the clock signal internal to or provided to the electrical component is reduced or halted to provide a decrease in power consumption.

A low power mode is provided for other electrical components using the design or inherent characteristics of the electrical components. For example, a field programmable gate array, such as a random access memory based field programmable gate array, has an initial unprogrammed state for receiving instructions and then operates in a programmed state during the processing of data using the programmed instructions. Power consumption is less in the initial unprogrammed state. To enter a low-power mode or decreased power state, the field programmable gate array is placed into the unprogrammed state. For example, an Altera Flex 10 K field programmable gate array device is forced into an unprogrammed state by asserting a "configuration" input without loading any programming data. For processing and operating in a full power mode, program data is loaded into the field programmable gate array. Other devices that use less power during an intialization stage or other state may be operated in a similar manner for decreased power consumption. Additionally or alternatively, a clock frequency associated with such electrical components may be decreased to reduce power consumption. Likewise or alternatively, a suspend or standby mode may be incorporated into the electrical component by design.

Other methods or techniques may be used for reducing the power consumption of an electrical component to enter a low power mode or decreased power state. For example, a voltage supplied to an analog component, such as an analog amplifier, is reduced. A voltage regulator may include a control for reducing the output voltage. As another example, variable gain amplifiers may be set to a gain associated with less power consumption.

For further reduction in power consumption, a plurality of electrical components are operated in a reduced power state. For example, some or all of the electrical components in one or more subsystems are operated in a low power mode.

In one embodiment, data path electrical components and/or subsystems are operated in a low power mode. For example, one of the transmit beamformer 26, receive beamformer 28, B-mode detector 34, Doppler estimator 36, scan converter 32, display interface 16, or display 18 are operated in a low power mode. In one embodiment, the display 18 comprises a cathode ray tube monitor with a low power sleep mode. The display 18 turns off high power consuming circuitry when the display 18 is not in use. Where the display 18 comprises a flat panel display, a back lighting fluorescent light source is turned off to reduce power consumption by the display subsystem.

The ultrasound processing control may also include electrical components or subsystems operated in low power mode. For example, the control processor 20 includes a microprocessor placed in a suspend or standby mode. Local subsystem control components may also operate in a reduced power mode.

In other embodiments, electrical components and/or subsystems of both the ultrasound data path and processing control path are operated in a low power mode or decreased power state. In one embodiment, all of the electrical components of the ultrasound system 10 capable of operation in a low power state are placed in the low power state (i.e., components in a plurality of subsystems). In alternative embodiments, only a subset of such electrical components are operated in the decreased power state.

The low power mode or decreased power state is entered in response to activation by the user, user configuration of the ultrasound system 10 or time. Electrical components may be forced into the low power mode in response to one or more of the factors described herein.

In one embodiment, a freeze or low power mode button or selection is provided to the user. The user depresses the button or selects the low power mode with the user interface 22. In response, the selected subsystem, electrical component, or the entire system 10 is placed in a reduced power state. Ultrasonic information is not actively acquired or processed by electrical components, subsystems or the ultrasound system in the low power mode.

The ultrasound system 10, subsystems, or individual electrical components are placed in the low power mode in response to time. Where the electrical component, subsystem or ultrasound system is not used for a period of time, such as 20 seconds, the associated electrical components are placed in a reduced power state. Other time periods may be provided, such as one or more minutes, for changing modes or states.

In one embodiment, if the user interface 22 does not receive input over a certain period of time, such as one or more minutes, the ultrasound system 10 is considered to be not in use. The ultrasound system 10 generates an audio or visual warning that the system 10 will enter a low power state. If no further input is received from the user interface 22, the control processor 20, the display interface 16, the display 18, the acquisition module 14 or combinations thereof are placed in a low power mode. One or more electrical components may already be operating in the low power mode in response to any of the various information discussed herein.

Electrical components or subsystems are placed in the low power mode in response to user configuration. The user enters configuration information or selects various functions of the ultrasound system 10 with the user interface 22. For example, the user selects generation of B-mode images without Doppler estimations or Doppler spectral information. In response, the control processor 20 configures the signal processor 30 to generate B-mode information. The control processor 20 also places electric components of the Doppler estimator 36 and any spectral Doppler estimator in a low power mode since these subsystems are not being used. As another example, the user selects generation of images from stored ultrasound data. The stored ultrasound data is obtained by the control processor 20 and provided to the display interface 16. The control processor 20 places electrical components in the acquisition module 14 in a low power mode. Alternatively, the stored ultrasound data comprises polar coordinate formatted data. The control processor 20 provides the polar coordinate data to the scan converter 32. The control processor places electrical components of the transmit beamformer 26, receive beamformer 28 and/or signal processor 30 in a low power mode. As yet another example, the user configures the ultrasound system 10 to provide Doppler information without clutter filtering. The electrical components associated with clutter filtering in the Doppler estimator 36 are placed in a low power mode. Other configurations and associated electrical components or subsystems may be used, resulting in different electrical components or subsystems being placed in a reduced power state.

By placing the electrical components in the low power modes as described herein without switching off the power, the electrical components begin processing quickly and seamlessly. The user of the ultrasound system is not inconvenienced by a power-up or boot process before using any of the low power mode electrical components, subsystems or the ultrasound system 10.

The quick and seamless recovery of the electrical components from a reduced power state allows for even more efficient power consumption. For example, electrical components with excess processing bandwidth are placed in a low power mode during even short periods of non-use. In one embodiment, an electrical component is placed in a low power mode between acquisitions of frames of data during real time imaging. For example, some or all of the electrical components of the scan converter 32 are placed in a low power state while a frame of Doppler data is estimated. In another embodiment, an electrical component is placed in a low power mode between acquisitions of ultrasound data associated with individual scan lines. For example, the transmit beamformer 26 is not used while the receive beamformer 28 acquires data from an ultrasound transducer 12. During this period, the transmit beamformer 26 or a subset of electrical components of the transmit beamformer 26 is placed in a low power mode.

Use of the low power modes described herein reduces power consumption. Reductions in power consumption save energy costs. Where the power source 24 comprises a battery or other limited source of power, reductions in power consumption extend battery life or allow operation of the ultrasound system 10 with a lesser amount of power.

Further power reliability is provided by an uninterruptable power supply. For example, the power source 24 comprises an uninterruptable power supply, such as an uninterruptable power supply designed for use with personal computers or servers. The uninterruptable power supply includes a cord and plug for insertion into a standardized or other outlet. For example the power cord is inserted into a 120 volt or 220 volt single face outlet. Operation from an uninterruptable power supply allows the ultrasound system 10 to operate without an external power source.

When the power cord of the uninterruptable power supply is inserted into an outlet, power from the outlet is used to power the ultrasound system 10. When such an external source of power is unavailable or when the external source of power provides less power than is needed by the ultrasound system 10, the battery backup of the uninterruptable power supply provides the additional power needed by the ultrasound system 10. The ultrasound system 10 is immune to brief disruptions in the line voltage, and the power source 24 allows movement of the ultrasound system from one area to another without concern over having access to an outlet. The uninterruptable power supply also eliminates the need to power-up and/or re-boot the ultrasound system 10 after each move, eliminating delays.

Figure 3:
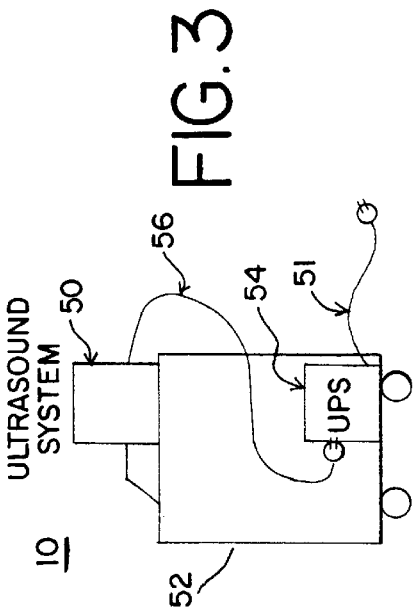
FIG. 3 is a graphical representation of one embodiment of an ultrasound scanner powered by an uninterruptable power supply.

FIG. 3 shows an ultrasound configuration generally at 10. The ultrasound system 10 includes an ultrasound system 50, a cart 52 and an uninterruptable power supply 54, a system power input cord 56 and an uninterruptable power supply power input cord 58. The ultrasound system 50 is positioned on the cart 52 with the uninterruptable power supply 54. The system power cord 56 plugs into the uninterruptable power supply 54. The uninterruptable power supply power cord 58 is adapted for insertion into an external outlet. The ultrasound system 50 and uninterruptable power supply 54 may be hardwired together or connected through a removable plug. In alternative embodiments, the uninterruptable power supply 54 and ultrasound system 50 connect to each other and in parallel with the external power source.

In one embodiment, the ultrasound scanner 50 comprises a portable ultrasound scanner. The uninterruptable power supply 54 is housed within or separate from the ultrasound scanner 50. For example, a hand-held portable ultrasound scanner that includes an uninterruptable power supply within a single casing is provided. In this embodiment, the ultrasound scanner preferably draws less than 100 watts of power under normal operation. Using the power consumption reduction techniques discussed above, less power may be used during operation. In alternative embodiments, more power is used. In this embodiment, the uninterruptable power supply 54 comprises a standard personal computer type uninterruptable power supply and is capable of providing power for one-half an hour or more of usage.

While the invention has been described above by reference to various embodiments, it will be understood that many changes and modifications can be made without departing from the scope of the invention. For example, additional methods or electrical components for reducing power consumption through low power mode operation may be used. Low power mode embodiments may be used independent of an uninterruptable power supply or other type of power source.

It is therefore intended that the foregoing detailed description be understood as an illustration of the presently preferred embodiments of the invention, and not as a definition of the invention. It is only the following claims including all equivalents that are intended to define the scope of the invention.

What is claimed is:

1. A medical diagnostic ultrasound system for reducing power consumption, the system comprising:
    an ultrasound data path comprising at least a first electrical component;
    an ultrasound processing control operatively connected with the ultrasound data path and comprising at least a second electrical component; and
    a source of power operatively connected with the ultrasound data path and the ultrasound processing control;
    wherein at least one of the first and second electrical components has a full power mode during use and a low power mode during at least one non-use period.

2. The system of claim 1 wherein the system comprises a portable ultrasound system.

3. The system of claim 1 wherein the at least one of the first and second electrical components comprises the first electrical component.

4. The system of claim 3 wherein the first electrical component comprises a beamformer component.

5. The system of claim 3 wherein the first electrical component comprises a signal processor component.

6. The system of claim 3 wherein the first electrical component comprises a scan converter component.

7. The system of claim 5 further comprising Doppler estimation components;
    wherein the signal processor component comprises a B-mode detector component, the B-mode detector component being in the low power mode and the Doppler estimation components being in the full power mode.

8. The system of claim 5 further comprising B-mode detection components;
    wherein the signal processor component comprises a Doppler estimation component, the Doppler estimation component being in the low power mode and the B-mode detection component being in the full power mode.

9. The system of claim 3 wherein the ultrasound data path comprises a plurality of sub-systems, at least a first sub-system in the full power mode at a first time and at least a second sub-system in the low power mode at the first time.

10. The system of claim 3 wherein the ultrasound data path consists of a plurality of sub-systems each in a low power mode at a same time.

11. The system of claim 1 wherein the at least one of the first and second electrical components comprises the second electrical component.

12. The system of claim 11 wherein the second electrical component comprises a processor.

13. The system of claim 1 further comprising a clock input to the at least one of the first and second electrical components, the clock input providing a reduced frequency signal during the low power mode.

14. The system of claim 13 wherein the reduced frequency signal comprises a constant signal.

15. The system of claim 1 wherein the at least one of the first and second electrical components comprises a field programmable gate array, the field programmable gate array being in an unprogrammed state for the low power mode.

16. The system of claim 1 wherein the at least one of the first and second electrical components comprises a component with a sleep-mode input, the low and full power modes responsive to a signal at the sleep-mode input.

17. The system of claim 1 wherein the at least one of the first and second electrical components comprises a digital component.

18. The system of claim 1 wherein the at least one of the first and second electrical components comprises an analog component.

19. The system of claim 1 wherein the at least one non-use period comprises a period reoccurring substantially at a frame rate.

20. The system of claim 1 wherein the low power mode is entered in response to a time period.

21. The system of claim 1 wherein the low power mode is entered in response to a configuration of the system.

22. The system of claim 1 wherein the source comprises an uninterruptable power supply.

23. The system of claim 1 wherein the source comprises a battery.

24. In a medical diagnostic ultrasound system for generating data for an ultrasound image of a region of a patient with a plurality of electrical components, the plurality of electrical components comprising a transmit beamformer, a receive beamformer, at least one signal processor and a scan converter, the improvement comprising:
    a power mode control path operatively connected with at least one of the plurality of electrical components, the at least one of the plurality of electrical components responsive to a signal from the power mode control path to change between a decreased-power state and an increased-power state, both the increased- and decreased-power states different than an off state.

25. The system of claim 24 wherein the system comprises a portable ultrasound system.

26. The system of claim 24 wherein the at least one of the plurality of electrical components comprises a beamformer component.

27. The system of claim 24 wherein the at least one of the plurality of electrical components comprises a signal processor component.

28. The system of claim 24 wherein the at least one of the plurality of electrical components comprises a scan converter component.

29. The system of claim 24 wherein the signal corresponds to entering the decreased power state and is provided to at least one of a plurality of sub-systems comprising the transmit beamformer, receive beamformer, at least one signal processor and scan converter is at a first time and at least another the plurality of sub-systems is in the increased power state at the first time.

30. The system of claim 24 wherein each of the transmit beamformer, receive beamformer, at least one signal processor and scan converter are in the decreased power state at a same time.

31. The system of claim 24 wherein the power mode control path comprises a clock input to the at least one of the plurality of electrical components, the clock input providing a reduced frequency signal during the decreased power state.

32. The system of claim 24 wherein the at least one of the plurality of electrical components comprises a field programmable gate array, and the power mode control path comprises a configuration input to the field programmable gate array, the field programmable gate array being in an unprogrammed state for the decreased power state.

33. The system of claim 24 wherein the signal changes at least about at a frame rate.

34. The system of claim 24 wherein the signal is provided in response to a configuration of the system.

35. The system of claim 24 further comprising a battery operable to provide power to the at least one of the plurality of electrical components.

36. A medical diagnostic ultrasound method for reducing power consumption by an ultrasound system, the method comprising the acts of:

(a) generating an ultrasound image with the ultrasound system;

(b) placing at least one component of an ultrasound data path of the ultrasound system in a low-power state.

37. The method of claim 36 wherein (b) comprises changing a clock frequency.

38. The method of claim 36 wherein (b) comprises configuring the at least one component into an unprogrammed state.

39. The method of claim 36 wherein (b) comprises transmitting a sleep signal.

40. The method of claim 36 wherein (a) is performed at a different time than (b) and the at least one component of the ultrasound system comprises two or more of a transmit beamformer, a receive beamformer, a signal processor and a scan converter.

41. The method of claim 36 wherein (a) is performed at a same time as (b) and the at least one component of the ultrasound system comprises one or more of a transmit beamformer, a receive beamformer, a signal processor, a B-mode detector, a Doppler estimator and a scan converter.

42. The method of claim 41 further comprising:

(c) performing (b) in response to a configuration.

43. The method of claim 41 further comprising:

(c) performing (b) in response to unused bandwidth.

44. The method of claim 36 further comprising:

providing power to the ultrasound system with a battery.

45. A medical diagnostic ultrasound configuration for uninterrupted power supply, the ultrasound configuration comprising:

an ultrasound system comprising an ultrasound beamformer and an ultrasound signal processor;

a power input operatively connected with the ultrasound system; and an uninterruptable power supply operatively connected with the power input.

46. The ultrasound configuration of claim 45 wherein the ultrasound system comprises a hand carriable portable ultrasound system.

47. The ultrasound configuration of claim 45 further comprising a cart, wherein the ultrasound system and the uninterruptable power supply are positioned on the cart and the power input operatively connects with the uninterruptable power supply.

48. The ultrasound configuration of claim 47 further comprising a power cord operatively connected with the uninterruptable power supply and adapted for insertion into a standard power outlet.

49. The ultrasound configuration of claim 45 wherein the uninterruptable power supply comprises a battery.

50. The ultrasound configuration of claim 45 wherein the ultrasound system draws less than 100 Watts.

51. A medical diagnostic ultrasound method for uninterrupted power supply to an ultrasound system, the ultrasound method comprising the acts of:

(a) powering the ultrasound system comprising an ultrasound beamformer and an ultrasound signal processor;

(b) powering an uninterruptable power supply from a power outlet; and (c) powering the ultrasound system with the uninterruptable power supply.

52. The ultrasound method of claim 51 further comprising:

(d) adapting the ultrasound system for hand carrying portability.

53. The ultrasound method of claim 51 further comprising:

(d) positioning the ultrasound system and the uninterruptable power supply on a cart.

54. The ultrasound method of claim 51 further comprising:

(d) plugging the uninterruptable power supply into a standard power outlet.

55. The ultrasound method of claim 51 wherein (b) comprises charging a battery of the uninterruptable power supply.

56. The ultrasound method of claim 51 further comprising:

(d) drawing less than 100 Watts with the ultrasound system.

* * * * *